United States Patent
Hogan et al.

(10) Patent No.: US 6,406,738 B1
(45) Date of Patent: Jun. 18, 2002

(54) POWDER COATING COMPOSITION FOR ELECTROSTATIC COATING OF PHARMACEUTICAL SUBSTRATES

(75) Inventors: John E. Hogan, Faversham; Trevor Page, Southampton; Linda Reeves; John N. Staniforth, both of Bath, all of (GB)

(73) Assignee: Phoqus Limited, West Malling (GB)

( * ) Notice: Subject to any disclaimer, the term of this patent is extended or adjusted under 35 U.S.C. 154(b) by 0 days.

(21) Appl. No.: 08/966,582

(22) Filed: Nov. 10, 1997

Related U.S. Application Data

(63) Continuation of application No. PCT/GB96/01101, filed on May 8, 1996.

(30) Foreign Application Priority Data

May 9, 1995 (GB) .............................................. 9509347
Oct. 5, 1995 (GB) .............................................. 9520302

(51) Int. Cl.$^7$ ........................... B01J 13/00; B01J 13/22; B05D 1/22
(52) U.S. Cl. ...................... 427/2.14; 427/189; 427/212; 427/201; 427/562; 427/460; 427/461; 427/469; 427/202; 427/203; 427/289; 427/424; 427/128; 427/129; 427/130
(58) Field of Search ................................. 427/189, 2.14, 427/212, 201, 562, 460, 461, 469, 202, 203, 289, 424, 128, 129, 130

(56) References Cited

U.S. PATENT DOCUMENTS

| | | |
|---|---|---|
| 2,698,814 A | 1/1955 | Ransburg |
| 3,764,538 A | 10/1973 | Shelffo |
| 3,900,000 A | 8/1975 | Gallen .................. 118/630 |

(List continued on next page.)

FOREIGN PATENT DOCUMENTS

| | | |
|---|---|---|
| DE | 2 247 701 | 4/1974 |
| DE | 3049179 A1 | 7/1982 |
| EP | 0 020 181 | 12/1980 |
| EP | 0 063 014 | 10/1982 |
| EP | 0 107 557 A1 | 5/1984 |
| EP | 0 164 959 A2 | 12/1985 |
| EP | 0 220 670 A2 | 5/1987 |
| EP | 0 277 741 A1 | 8/1988 |
| EP | 0 307 642 A2 | 3/1989 |
| EP | 0 452 862 A2 | 10/1991 |
| EP | 0 459 048 | 12/1991 |
| EP | 0 536 791 A1 | 4/1993 |
| EP | 0 543 541 A1 | 5/1993 |
| EP | 0 551 700 A1 | 7/1993 |
| EP | 0 567 201 A2 | 10/1993 |
| EP | 0 607 009 A1 | 7/1994 |
| EP | 0 661 091 A1 | 7/1995 |

(List continued on next page.)

OTHER PUBLICATIONS

Chemical Abstracts, vol. 120, No. 20, (1994), Grosvenor M.P. Diss. Abstr. Int., vol. 53, No. 7 (1991) Bath, p. 3492, Grosvenor M.P.
Kirk–Othmer, Encyclopedia of Chemical Technology, 3 ed., vol. 19, pp. 1–2 (1982).
U.S. published Patent Application 2001/0018098 Pletcher et al.

*Primary Examiner*—Shrive P. Beck
*Assistant Examiner*—Jennifer Kolb Michener
(74) *Attorney, Agent, or Firm*—Nixon & Vanderhye

(57) ABSTRACT

A method of coating a substrate which is a core for a pharmaceutical dosage form, which comprises electrostatically applying to a surface of the core a powder material comprising active material, the coating material applied constituting a dosage of active material, wherein the powder material includes composite particles, each composite particle comprising two or more components having different physical and/or chemical properties.

238 Claims, 2 Drawing Sheets

U.S. PATENT DOCUMENTS

Figure 1:
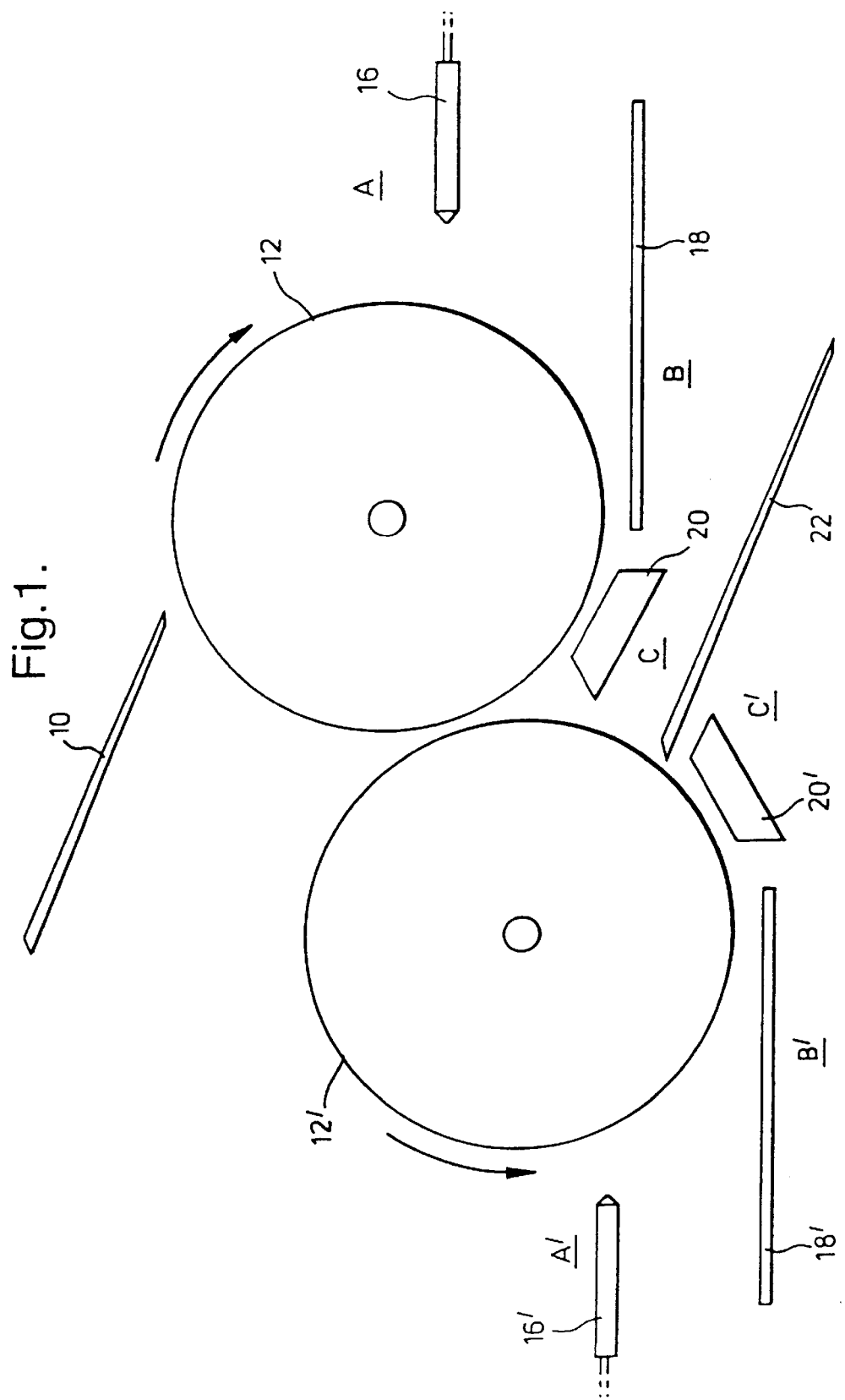

| | | | |
|---|---|---|---|
| 4,128,445 A | | 12/1978 | Sturzenegger et al. |
| 4,176,175 A | | 11/1979 | Maekawa et al. ............. 424/35 |
| 4,197,289 A | | 4/1980 | Sturzenegger et al. |
| 4,201,834 A | * | 5/1980 | Hannon et al. ............. 427/195 |
| 4,322,449 A | | 3/1982 | Voss et al. |
| 4,349,531 A | * | 9/1982 | Mlodozeniec et al. ........ 424/27 |
| 4,359,483 A | | 11/1982 | Kaetsu et al. |
| 4,433,076 A | | 2/1984 | Bauer et al. ................. 523/342 |
| 4,454,125 A | * | 6/1984 | Demopoulos ............... 424/201 |
| 4,482,387 A | | 11/1984 | Wood et al. ................. 106/270 |
| RE31,764 E | | 12/1984 | Voss et al. |
| 4,547,571 A | | 10/1985 | Mukohyama et al. ......... 536/90 |
| 4,548,825 A | | 10/1985 | Voss et al. |
| 4,704,295 A | | 11/1987 | Porter et al. ................. 424/440 |
| 4,786,505 A | * | 11/1988 | Lovgren et al. ............ 424/468 |
| 4,800,079 A | | 1/1989 | Boyer |
| 4,810,501 A | * | 3/1989 | Ghebre-Sellassie et al. 424/469 |
| 4,828,840 A | | 5/1989 | Sakamoto et al. |
| 4,925,670 A | | 5/1990 | Schmidt |
| 4,935,246 A | | 6/1990 | Ahrens |
| 4,994,273 A | * | 2/1991 | Zentner et al. ............. 424/422 |
| 5,011,694 A | * | 4/1991 | Nuernberg et al. ......... 427/336 |
| 5,076,706 A | * | 12/1991 | Shibuya et al. ............. 366/349 |
| 5,206,030 A | | 4/1993 | Wheatley et al. ........... 424/490 |
| 5,320,796 A | * | 6/1994 | Harashima et al. ......... 264/349 |
| 5,411,730 A | * | 5/1995 | Kiroptin et al. ............ 424/322 |
| 5,436,026 A | * | 7/1995 | Berta ......................... 427/2.14 |
| 5,470,603 A | * | 11/1995 | Staniforth et al. ......... 427/2.14 |
| 5,474,786 A | | 12/1995 | Kotwal et al. |
| 5,540,995 A | * | 7/1996 | Kitano et al. .............. 427/2.14 |
| 5,714,007 A | * | 2/1998 | Pletcher et al. ............. 118/629 |
| 5,792,513 A | * | 8/1998 | Koslow et al. ............. 427/195 |
| 5,846,595 A | * | 12/1998 | Sun et al. ................... 427/2.14 |
| 6,026,809 A | | 2/2000 | Abrams et al. |
| 6,117,479 A | * | 9/2000 | Hogan et al. ............... 427/2.14 |
| 6,294,024 B1 | | 9/2001 | Sun et al. |
| 6,298,847 B1 | | 10/2001 | Datta et al. |
| 6,319,541 B1 | | 11/2001 | Pletcher et al. |

FOREIGN PATENT DOCUMENTS

| | | |
|---|---|---|
| EP | 0 678 564 A3 | 10/1995 |
| GB | 1075404 | 7/1967 |
| GB | 1108837 | 4/1968 |
| GB | 1 561 100 | 2/1980 |
| GB | 2 056 885 A | 3/1981 |
| GB | 2 065 691 A | 7/1981 |
| GB | 2 129 301 A | 5/1984 |
| GB | 2 179 254 A | 3/1987 |
| GB | 2 203 336 A | 10/1988 |
| GB | 2 241 889 A | 9/1991 |
| GB | 2 253 164 A | 9/1992 |
| LU | 52460 | 6/1968 |
| WO | 91/16041 | 10/1991 |
| WO | 92/11002 | 7/1992 |
| WO | 92/14451 | 9/1992 |
| WO | 94/05263 | 3/1994 |
| WO | 94/11446 | 5/1994 |
| WO | 96/02236 | 2/1996 |
| WO | 96/11707 | 4/1996 |
| WO | 96/39256 | 12/1996 |
| WO | 96/39257 | 12/1996 |
| WO | 97/04827 | 2/1997 |
| WO | 97/37775 | 10/1997 |
| WO | 97/37803 | 10/1997 |
| WO | 97/38480 | 10/1997 |
| WO | 97/47346 | 12/1997 |
| WO | 97/47347 | 12/1997 |
| WO | 99/06593 | 2/1999 |
| WO | 99/06814 | 2/1999 |
| WO | 99/13817 | 3/1999 |

* cited by examiner

POWDER COATING COMPOSITION FOR ELECTROSTATIC COATING OF PHARMACEUTICAL SUBSTRATES

This is a continuation of PCT application No. PCT/GB96/01101, filed May 8, 1996.

This invention relates to the electrostatic coating of pharmaceutical substrates with a powder coating material and to powder coating materials for coating the pharmaceutical substrates. In particular, but not exclusively, the invention relates to the electrostatic coating of cores of pharmaceutical tablets with a powder coating material and to powder coating materials for coating the cores of pharmaceutical tablets. While reference is made throughout the specification to pharmaceutical tablets and the invention is of particular application to pharmaceutical tablets of conventional shape, it should be understood that the term is to be interpreted in a broad sense as covering also other products to be taken orally such as pellets, capsules or spherules.

Electrostatic coating of electrically conducting substrates such as metal objects is well known. For example in certain paint spraying processes, paint is electrically charged and droplets of paint are sprayed onto an earthed metal object. Such methods have been successful in obtaining a uniform coating on the substrate.

Electrostatic coating of electrically non-conducting substrates, and pharmaceutical tablet cores in particular, is more difficult. There have been proposals for electrostatic coating of tablets for many years. For example, GB 1 075 404 proposes an apparatus for coating tablets in which an atomiser is used to spray finely divided particles of a coating solution onto tablets in a high potential field. The coating is dried using, for example, an infra-red heater. Such proposals have not however been practised on any substantial commercial scale and the coating of pharmaceutical tablet cores is most commonly carried out as a batch process by applying a liquid coating in a revolving drum. The liquid coating material may of course be supplied in some cases in powder form but, if so, it is then dissolved or dispersed in a liquid prior to application. It is not, therefore, applied to the tablet core in powder form.

It is in many ways easier to apply a liquid rather than a powder coating to the core of a pharmaceutical tablet. It is difficult to obtain adhesion of the powder to the tablet and in order to secure the coating to the core, the powder must be transformed into a film without damaging the tablet core, which usually will include organic materials. Furthermore an even coating is required and it is difficult to obtain an even coating of powder on a tablet core.

When a liquid coating is used, the coating must be dried. Theoretically such drying could in some circumstances be carried out at room temperature but in commercial practice it is important, for example because of the rate at which the process must be carried out, to heat the tablets and that is expensive because of the large input of energy required to vaporise the solvent used in the liquid coating. Another disadvantage of liquid coating is that it cannot be used for coating materials that are not soluble or suitably dispersible in a usable liquid, preferably water.

WO92/14451 is concerned with electrostatic powder coating of pharmaceutical tablets and describes and illustrates a process in which the cores of pharmaceutical tablets are conveyed on an earthed conveyor belt and electrostatically charged powder is sprayed towards the cores to form a powder coating attached to the surfaces of the cores. The powder coating is then fused to give a fused film coating secured to the core.

A disadvantage of such a method is that the majority of the powder sprayed towards the cores is not charged and is not deposited on the cores. That leads to overspray and to wastage of the powder material and makes it difficult to obtain a uniform coating.

In a first aspect, the present invention seeks to provide a powder coating material suitable for use in the electrostatic powder coating of a pharmaceutical tablet core and to provide a method for the electrostatic coating of a pharmaceutical tablet core in which a special powder coating material is used to facilitate the electrostatic coating.

The first aspect of the invention provides a powder coating material for use in the electrostatic powder coating of a tablet core, especially for use in a coating method as defined below, and having special properties to make it suitable for use in such a method. The special properties which the powder coating material advantageously has are further defined below and where the advantages provided by those properties are dependent upon the coating method employed, that method is also further defined.

According to a first aspect of the invention there is provided a powder coating material suitable for use in the electrostatic powder coating of a pharmaceutical tablet core in which the material is pharmaceutically acceptable, is treatable to form a film coating and includes composite particles, the composite particles comprising two or more components having different physical and/or chemical properties.

It is important that the powder coating material is a pharmaceutically acceptable material. That in itself imposes severe constraints on the powder coating material since at least most powder coating materials that are commercially available for use in electrostatic powder coating processes are not physiologically tolerable or pharmaceutically acceptable and materials that are commercially available for use as coating materials for pharmaceutical tablet cores are not in a form suitable for electrostatic powder application because other properties of the material are not suitable.

The powder coating material of the invention includes at least two different components, each different component having different physical and/or chemical properties. It is much simpler to provide a powder material having the desired properties referred to above and elsewhere in the specification by providing a material composed of more than one component than by providing a single component material. For powder materials including two or more different components, we have found that improved coatings may be achieved where the powder includes composite particles of the components.

It is particularly important for the particles of the coating material to include more than one of the components where one or more of the components do not have the necessary electrical properties to become coated onto the core when, for example, the method of coating used is as described in the example below. Where the particles are not composite particles those particles of components that do not have the necessary electrical properties may simply remain at the source of powder and will not become coated onto the tablet core. The inclusion of the composite particles is thought to improve the efficiency of coating of the substrate as well as the uniformity of coating applied. The improved efficiency of coating can help to reduce the time required for coating each substrate.

The term "composite particles" as used in this specification refers to particles which have been formed from two or more different components. The composite particles are not homogeneous, that is they have two or more regions each comprising different components of the particle. The composite particle may have the form of a discrete composite particle or may be in the form of agglomerates or aggregates of discrete particles of the different components, the agglomerates or aggregates behaving as discrete composite particles.

Advantageously at least 50% by weight of the particles of the powder are composite particles. Ideally, substantially all of the particles are composite particles but that may not be feasible, in particular where the particle size of the composite particle is small. Where the powder includes more than two components having different physical and/or chemical properties, advantageously the composite particle also includes those other components. Ideally, substantially all of the composite particles would comprise discrete particles including each of the different components. However, in practice, satisfactory coatings can be achieved where the individual component particles are formed into the composite particle as aggregates or agglomerates.

Advantageously, the two or more components have be co-processed. The co-processing may comprise granulation, spray congealing, spray drying or co-milling. Where the method of co-processing results in particles of a relatively large size, for example in the case of granulation, in some cases it would be advantageous to perform a subsequent milling step to reduce the particle size. Alternatively, a micronising step may be performed.

As will be understood, blending powder components together will usually form an ordered mix of the components. However, in special cases, by careful selection of the blending conditions, for example the initial particle sizes of the components and the blending method, composite particles may be obtained by a blending method.

In accordance with the first aspect of the invention, the powder coating material is one which, after it has coated the surface of the tablet core, can be treated to form a film coating secured to the core. Thus the method of coating advantageously includes the step that, after the surface of the tablet core has been coated with the powder, the powder is treated to form a film coating secured to the tablet core. The film coating is advantageously continuous, in that it is not divided into separate parts, but there may be small gaps, not visible to the naked eye, for example between particles of coating that have become secured to one another during the treatment step. Thus the coating may be sintered. For certain applications it is preferred that the film coating is free of any gaps and/or is substantially homogeneous.

When the powder material is first deposited on the tablet core it is in most cases only weakly adhered to the surface of the substrate and is easily dislodged. Treatment to form a film coating is especially advantageous when coating a pharmaceutical tablet core because the core itself is likely to be of low mechanical strength and the film coating can be used to impart strength and make the coated tablets more resistant to subsequent processing such as packaging and opening of packages. The film coating, although it may impart extra strength to the tablet core, will often be very weak when isolated from the surface of the core. The tensile strength of the film coating as a free film may be, for example, 8 $MNm^{-2}$ or even lower, and the tensile strength is found to decrease with the increase of the amount of $TiO_2$ in the coating material.

In the cases where the tensile strength of the free film is low, it is especially important for the film to be a coherent coating on the surface of the tablet core with good adhesion to the core.

Where the powder material is transformed into a liquid phase during the formation of the film coating it is preferable that the viscosity of the powder material when in the liquid phase is less than 500 Pas, more preferably 75 Pas.

Advantageously, the powder coating material is treatable at a temperature of less than 250° C., more preferably less than 200° C., to form a film coating. Advantageously, the powder coating material is fusible at atmospheric pressure at a temperature of less than 250° C., more preferably less than 200° C. It is important that the powder can be treated to form a coating around the tablet core without damaging the tablet core and that imposes a demand on the material because of the sensitivity to heat of most tablet cores, which contain organic materials. Preferably the powder coating material has a melting point in the range of 50° C. to 180° C., more preferably in the range of from 60° C. to 100° C. For a material exhibiting a glass transition, the powder coating material preferably has a softening point in the range of 30° C. to 180° C.

The above requirements place further restrictions on the powder coating material. Many materials are not fusible and would char on the application of heat. Other materials, although they may be fusible, require a long exposure to the heat source for fusing to occur such that the risk of damage to the core is significantly increased and the time taken to form the film on the core is unacceptable for economic reasons.

The desired temperature at which the powder coating material is treatable will of course depend on the material making up the tablet core and for some materials it may be possible for the treatment step to involve temperatures above 250° C. In such cases, the duration of exposure to such high temperatures will be short.

The treatment of the powder to form a film coating preferably involves a heating step, preferably using infra red radiation, but other forms of electromagnetic radiation or conduction or induction may be used. Also the treatment of the powder material may be achieved partly or wholly by reducing the pressure of the environment of the tablet core. The change in the powder material during the treatment may simply be a physical change from a solid to a liquid and then, on cooling, to a continuous solid film. Alternatively, the powder material may include a polymer which is cured during the treatment, for example by irradiation with energy in the gamma, ultra violet or radio frequency bands, to form a cross-linked polymer film.

We have found that the particle size of the powder coating material also has an especially important effect on the behaviour of the material in an electrostatic powder coating method. Advantageously the material has a small particle size. Preferably at least 95% by number and preferably at least 90% by volume of the particles of the powder material have a particle size less than 50 μm. The term "particle size" refers to the equivalent particle diameter of the particles and may be measured using, for example, laser light diffraction.

Where the relevant particle is a composite particle comprising an agglomerate or aggregate of particles, the particle size is that of the composite particle and not of the individual particles in the agglomerate or aggregate.

Such a particle size is surprisingly small for a coating material for a pharmaceutical tablet core and indeed such small particle sizes are recognised as having disadvantages such as making the material more difficult to produce and to handle by virtue of its cohesiveness. We have found, however, that for coating pharmaceutical tablet cores in an electrostatic process there are special benefits in adopting a small particle size and the benefits more than counter the disadvantages. For example, the high surface to mass ratio provided by a small particle increases the electrostatic forces on the particle in comparison to the inertial forces. Increasing the electrostatic forces has the benefit of increasing the force on a particle that causes it to move into contact with the tablet core whilst a reduction in the inertia reduces the force needed to accelerate a particle and reduces the likelihood of a particle arriving at the tablet core bouncing back off the core. We have found that it is especially advantageous if at least 90% by volume of the particles of the powder material have a particle size of less than 20 µm. Preferably at least 95% by number of the particles of the powder material have a particle size of less than 30 µm.

Especially in the case where for a chosen powder material it is found that there is a tendency for the particles to bounce back from a surface of the tablet core, a pretreatment composition may be applied to a surface of the tablet core, before the core is supported adjacent to the source of powder material. The pretreatment composition can improve the capture of particles by the surface of the core and can enable larger particles, even as large as 750 µm, to be used as the coating material. The pretreatment composition may be a liquid and may increase the forces acting on the particles to hold them on the core. Where a pretreatment is used, preferably at least 90% by number of the particles have a size less than 300 µm, and preferably at least 50% by number of the particles have a size less than 200 µm.

If the particle size is reduced too far, the difficulties associated with handling the powder become severe. Accordingly, it is advantageous that at least 50%, preferably at least 75%, most preferably 90%, by volume of the powder has a particle size of at least 5 µm.

In one preferred powder coating material, the mean particle diameter is about 10 µm with substantially no particles having a diameter greater than 100 µm.

Preferably, at least 30% by volume of the particles of the powder have a particle size in the range of from 5 µm to 25 µm.

We have found that it is also particularly important for the particles of the powder to have a narrow range of particle size. Preferably at least 30%, more preferably at least 75% by weight of the particles have a particle size which lies in a range of from x to 2x, more preferably in a range of from x to 1.5x, most preferably in a range of from x to 1.25x where x represents a size of particles in the powder.

For example, for a powder having particles of a relatively small size, preferably at least 30% by weight of the particles have a particle size which lies in a range of from 10 µm to 20 µm, more preferably in a range of from 10 µm to 15 µm and most preferably in a range of from 10 µm to 12.5 µm.

Where the particles are of a relatively large size, for example where a pretreatment is to be used as described above, the preferred relative variation in particle size will generally be less than for particles of relatively small size.

We have found that, with regard to the achievement of a good uniform application of the powder to the tablet cores, and from core to core, powders in which there is a large range of particle size are disadvantageous relative to those powders in which the range of particle size is small. That is thought to be because particles having a certain particle size are preferentially coated onto the tablet core compared with particles of smaller or larger size. This can lead to inhomogeneity of the coating of the core and variations in the quality of coating from one coated core coated from a newly introduced batch of coating material to another coated core coated later from the same batch.

Advantageously, the powder coating material has a moisture content (measured by moisture loss on drying) of not more than 10%, preferably less than 5%, more preferably not more than 3% by weight based on the weight of the powder coating material.

There are various different electrostatic effects which may be used in an electrostatic process for coating a pharmaceutical tablet core with a powder in accordance with the first aspect of the invention and various different electrical properties of the powder that are especially well suited for the use of the different effects. Three different effects and associated properties of the powder will now be described and it should be appreciated that each may be employed independently of or in conjunction with one or more of the others.

A first possibility is to induce a temporary dipole in a particle of powder, the particle then being caused to be directed towards the tablet core by the interaction of the dipole and the electric field in the region between the source of powder and the tablet core. The coating material preferably has a resistivity in the range of $10^8$ to $10^{16}$ $\Omega$m.

A second possibility is to apply a net charge to a particle of powder. The net charge may be introduced triboelectrically or by corona charging. The coating material is therefore preferably receptive to such a net charge and able to retain the charge (sufficiently long for the material to be directed onto the tablet core).

A third possibility is to provide a permanent dipole, or a quasi-permanent dipole, in a particle of powder. Such an "electret" is then able to be directed towards the tablet core by interaction with the electric field in the region between the source of powder and the tablet core. Thus the coating material may comprise an electret.

A fourth possibility is to provide a magnetic dipole in a particle of powder using iron or other magnetic or paramagnetic material.

It is preferable that the powder material can be directed towards the tablet core without relying on any overall net charge being applied to the powder material and without relying on any permanent implanted charge in the powder material. Thus it is preferred that the powder material is susceptible to movement under the action of electrostatic forces, the susceptibility being determined by the test defined below.

To determine whether or not a powder material is susceptible to movement under the action of electrostatic forces, the following test should be conducted:

A sample of 0.5 g of the powder material is taken and placed on an electrically conducting horizontal metal plate maintained at earth potential in an environment having a relative humidity of not more than 65%. The powder material is spread to a thickness approaching a monolayer. After leaving the powder material in the environment for 30 minutes, an electrically conducting spherical metal probe of diameter 5 mm is positioned 10mm above the centre of the powder material and a high voltage potential first of +10 kV and then of −10 kV (with current limited to about 5 µA) is then applied to the probe for about 10 s. If particles of powder material representative of the material as a whole are drawn upwards into contact with the probe during the application of either high voltage potential, then the test result is that the powder material is susceptible to movement under the action of electrostatic forces; if particles of powder are not drawn upwards into contact with the probe, or if only certain kinds of particle are drawn up so that the particles drawn up are not representative of the material as a whole, then the test result is that the powder material is not susceptible to movement under the action of electrostatic forces.

The susceptibility of the powder material will of course depend on a combination of the electrical properties of the powder and other physical properties such as the size of the particles in the powder.

To the extent that the particles of coating material become charged (for example, triboelectrically) before becoming attached to the surfaces of the cores, it is particularly advantageous for the particles to be substantially all of the same sign of charge. We have found that where a cloud of particles contains a mixture of positive and negative charges, a less satisfactory coating is produced on the core surface. Thus it is advantageous for the powder to be of a composition such that, if the powder becomes charged, substantially all the particles are of the same sign of charge. Furthermore, if the particles are not the same sign of charge there is more overspray of the powder material thus decreasing the efficiency of the coating process. Preferably, most of the particles will also have substantially the same magnitude of charge.

Since the material comprises more than one component, the properties of the powder material may be altered by adjusting the relative proportions of the components. In general where reference is made to a property of the powder material it is the property exhibited by the material as a whole that is being referred to and it may be that one or more components of the material do not on their own exhibit that property. It may also be satisfactory, however, if only one or some of the components of the powder coating material, and not the material as a whole, exhibit the property referred to: for example, the benefit of the material forming a film coating at a low temperature may be achieved by only one of two or more components of the material exhibiting that property; the other component(s) may remain as solid particles and may represent a larger proportion by weight than the particles that are transformed into the film coating; in such a case, there may be a substantial variation in the particle sizes of the two components; for example, the particles that are transformed into the film coating may have a particle size in the range of 5 to 20 $\mu$m whilst the particles that remain as solid particles may be substantially larger.

One of the different components may serve to impart the necessary electrostatic properties to the powder material. For example, one different component may be charged triboelectrically and/or by corona charging, and/or may be an electret or magnet and/or may be susceptible to movement under the action of electrostatic forces, as defined by the test described herein.

The chemical properties of the powder material are also of importance in determining the effectiveness of the formation and the appearance of the coating.

When discussing the chemical properties of the material it is convenient to treat the material as composed of a plurality of components but, as will become clear from the description below, the same chemical compound may be employed as more than one component and therefore the reference in the description below to the powder material being composed of more than two components should not be regarded as requiring that more than two different components are necessarily present, except where the components are specifically referred to as being different.

Preferably the powder material includes a first component which is fusible to form a continuous film on the surface of the core, preferably at a temperature of less than 250° C., preferably less than 200° C. As discussed above, fusing may take the form of melting, softening or cross-linking of the first component within the temperature ranges indicated above.

Preferably the first component is substantially soluble in aqueous media. Usually the first component will be soluble in neutral aqueous media but it may be soluble in only a selected range of pH, for example pH3 to pH6 or pH8 to pH14.

The first component preferably comprises one or more of polyoxyethylenes, sugar alcohols and unsaturated or saturated fatty acids or esters. The first component may comprise a cellulose derivative fusible at a temperature below 250° C., for example hydroxy propyl cellulose. Not all cellulose derivatives are suitable for use as the first component, for example, hydroxypropyl methyl cellulose does not have the required fusing properties and chars on heating.

The first component may comprise polyethylene glycol which has good fusibility properties and, after treatment, can form a good continuous coat over the surface of the substrate.

The preferred sugar alcohol is xylitol, as that material has both suitable electrical properties and is fusible at a temperature suitable for use as the coating material in the coating of pharmaceutical tablet cores.

Other possible materials for the first component include waxes and oils or alcohols of waxes or oils, poloxamers, alkyl phthalates, for example diethylphthalate, citric acid or esters. Where a component of the powder is a liquid, the component may simply be added to other components in liquid form or may be present with, for example, a carrier material in powder form.

Clearly there are other compounds having suitable fusing properties and the above are given merely as examples.

The first component may consist of just one compound, or may include two or more compounds.

In many cases the component having the most desirable fusing properties will not have the most preferred electrical properties and/or will not be suitable for providing the desired finish, coverage or appearance of the coating. Accordingly, a second component is preferably provided having the required electrical properties as described above.

It will be understood that the first component may also have the desired electrical properties of the second component and that the second component may have the desired fusing properties of the first component.

The second component may, for example, comprise one or more of acrylic acid, polymers and co-polymers of acrylic acid and their derivatives, for example polymethyl acrylate, polyalkenes and their derivatives, including esters and arylesters and their derivatives, polyvinyl alcohols and esters, cellulose and its derivatives, for example cellulose ethers and cellulose esters (either cross-linked or uncross-linked) for example ethyl cellulose, and one or more enteric polymers for example cellulose acetate phthalate and hydroxypropyl methyl cellulose phthalate. The second component may include one or more biodegradable polymers, for example one or more of polylactides, polyglycolides, polyhydroxybutyrates, polyhydroxyvalyrate, ethylene vinyl acetate copolymers, and polyanhydrides (homo or hetero polymers). The second component may be polyethylene oxide.

As already described, it is possible for the first component and the second component to include the same compound or compounds, but in most cases the first and second components are different compounds. For example, the first and second components may each include xylitol but in such a case viscosity modifiers and crystalline inhibitors should also be added to provide the desired fusing properties for the second component.

The coating material including two or more different components, preferably also includes a dispersing component which improves the dispersion of the different components. The dispersing component is preferably a surfactant which may be anionic, cationic or non-ionic, but may be another compound which would not usually be referred to as a "surfactant" but has a similar effect. The dispersing component may be a co-solvent.

The dispersing component may be one or more of, for example, sodium lauryl sulphate, docusate sodium, Tweens (sorbitan fatty acid esters), poloxamers and cetostearylalcohol. The dispersing component may comprise the same compound or compounds as that of the first and/or the second components. As indicated above, both the third and first components may comprise poloxamers. Preferably, the material includes at least 1%, preferably from 2% to 5%, by weight of dispersing component, based on the weight of the material.

Advantageously, the powder coating material includes an anti-friction component to reduce the frictional and/or other forces between the particles of the powder coating material to improve the flowability of the powder. The anti-friction component may be titanium dioxide, colloidal silicon dioxide, talc or starch or a combination of those.

Where the coating material is used for "immediate" release tablets, the powder coating material advantageously includes a disintegrator which may disrupt the coating. In the case of a coating on a tablet core, the inclusion of the disintegrator in the coating facilitates the disintegration of the coating once the tablet has been ingested.

The disintegrator may be one which swells rapidly and extensively on contact with moisture, thereby disrupting the coating. Some disintegrators may swell to become up to 40 times their original volume within seconds. Examples of suitable disintegrators include sodium starch glycolate (cross-linked) and sodium carboxymethylcellulose (cross-linked).

Alternatively, or in addition, the disintegrator may be of a wicking-type which allows penetration of moisture through the coating to the tablet core, but which prevents moisture moving from the tablet core back through the coating, thereby causing rupture of the coating. Examples of suitable disintegrators of the wicking type include native starch, cross-linked polyvinyl pyrrolidone (crosprovidone).

The disintegrator may be a gas producing type, for example sodium carbonate, sodium hydrogen carbonate and sodium glycinate.

Preferably, the powder coating material contains less than 10% by volume of disintegrator. Preferably, the powder contains less than 5%, preferably less than 2%, more preferably less than 1%, most preferably about 0.5% by weight of disintegrator.

Preferably the powder coating material further includes one or more opacifiers, for example titanium dioxide and talc. Preferably the material comprises less than 50%, preferably less than 40%, more preferably less than 30% or less than 10% by weight of opacifiers based on the weight of the material.

Preferably the powder coating material further includes one or more colourants, for example metal oxides or lakes, for example aluminium lakes, iron oxide, dyes and may include one or more taste modifiers, for example aspartame, acesulfame k, cyclamates, saccharin, sugars and sugar alcohols or flavourings. Preferably the is material comprises less than 10%, preferably from 1 to 5% by weight of colourants based on the weight of the material and preferably less than 5%, more preferably less than 1% of flavouring based on the weight of the material. Where the flavouring is a sweetener, preferably the material comprises less than 0.5% by weight of sweetener. Preferably the material comprises less than 5% by weight of colourants and flavourings based on the weight of the material. It will be appreciated that the anti-friction component, the opacifier, the colourant and the taste modifier may comprise the same compound or compounds as that of another component of the powder coating material.

The powder coating material may include a biologically active material, that is a material which increases or decreases the rate of a process in a biological environment. The biologically active material may be one which is physiologically active. The coating material comprising active material may be applied to, for example, a tablet core containing the same or a different active material, or may be applied to a core containing no active material. The active material may include one or more compounds. The active material may include acid-peptic and motility influencing agents, laxatives, anti-diarrhoeials, colo-rectal agents, pancreatic enzymes and bile acids, antiarrhythmics, antianginals, diuretics, anti-hypertensives, anti-coagulants, anti-thrombotics, fibrinolytics, haemostatics, hypolipidaemic agents, anti-anaemia and neutropenia agents, hypnotics, anxiolytics, anti-psychotics, anti-depressants, anti-emetics, anti-convulsants, CNS stimulants, analgesics, anti-pyretics, anti-migraine agents, non-steroidal anti-inflammatory agents, anti-gout agents, muscle relaxants, neuro-muscular agents, steroids, hypoglycaemic agents, hyper-glycaemic agents, diagnostic agents, antibiotics, anti-fungals, anti-malarials, anti-virals, immunosuppressants, nutritional agents, vitamins, electrolytes, anorectic is agents, appetite suppressants, bronchodilators, expectorants, anti-tussives, mucolytics, decongestants, anti-glaucoma agents, oral contraceptive agents diagnostic and/or anti-neoplastic agents.

The tablet core to which the powder coating material is applied will usually comprise one or more inactive agents. The inactive agent may include diluents, for example including lactose, sucrose, dextrose, starch, cellulose, microcrystalline cellulose; binders, for example polyvinyl pyrrolidone, starch mucilage, gelatin, acacia, disintegrants, for example cross-linked sodium carboxymethyl cellulose, sodium starch glycollate, cross-linked polyvinyl pyrrolidone; lubricants, for example magnesium stearate, sodium stearyl fumarate; glidants, for example colloidal silica, talc; surfactants, for example wetting agents: sodium lauryl sulphate, docusate sodium; colourants; flavours and/or gas producers, for example sodium bicarbonate and citric acid.

The tablet core may also comprise one or more of the active materials listed above.

Preferably the powder coating material includes at least 0.5% by weight, more preferably 1% by weight, of active material based on the weight of the powder coating material. For example, a 10 mg coating on a tablet may contain approximately at least 0.05 mg of active material.

The proportions in which the components of the powder coating material are mixed is largely dependent on the materials comprising the powder coating material and the nature of the substrate to be coated. The proportions will be adjusted so that the desired electrical and fusing properties of the powder coating material are obtained. Usually, the powder coating material will contain at least 10%, preferably at least 15%, preferably about 20% by weight of the first component. Usually, the powder coating material will contain at least 10%, preferably at least 20%, and more preferably at least 40%, by weight of the second component, in each case based on the weight of the powder coating material. Preferably the ratio, by weight, of the second component to the first component is about 3:1. The ratio of the components depends on the material comprising the first and second components. The ratio may be 2:1 or 1:1.

The invention further provides a coating material for the electrostatic coating of a pharmaceutical substrate, the coating material including active material. As indicated above, the coating material comprising active material may be applied to, for example, a tablet core containing the same or a different active material, or may be applied to a core containing no active material.

Where very small doses of active material are to be administered in tablet form, the active material is mixed with a large volume of non-active "filler" material in order that a tablet of manageable size is produced. Hitherto, the active material and filler material have simply been blended together and doses of the resulting mixture tabletted. It has been found that it is very difficult to control accurately the amount of active material contained in each tablet, leading to poor dose uniformity. That is especially the case where the required amount of active material in each tablet is very low.

By applying active material to a surface of the tablet, it has been found to be possible to apply accurately very small amounts of active material to the tablet, leading to improved dose reproducibility.

The amount of active material contained in the coating material will, of course, depend on the size of the dose of the active material to be applied to the substrate and the thickness of the coating to be formed. Usually, the material includes at least 0.5% by weight of active material based on the weight of the coating material.

Advantageously, the coating material is a powder coating material. The coating material may therefore advantageously be applied using a method similar to that described above, thus the coating material may be applied to the substrate accurately and with little overspray.

Preferably, the coating material including the active material has at least 90% by number of particles having a particle size not more than 50 μm. Preferably at least 90% by number of the particles of the powder have a particle size less than 30 μm, more preferably less than 20 μm.

The invention also provides the use of a coating material comprising active material in the electrostatic coating of a substrate, especially in the electrostatic coating of a core of a pharmaceutical tablet.

The first aspect of the invention also provides a method of electrostatically coating a pharmaceutical tablet core with a powder material, the powder material being as defined above.

The first aspect of the invention further provides a powder coating material for use in the electrostatic coating of a substrate, the powder being obtainable by a method as described above.

The first aspect of the invention still further provides a pharmaceutical tablet comprising a tablet core and a powder coating material as defined above.

The first aspect of the invention further provides a method of coating a pharmaceutical tablet core with a powder, the method comprising supporting the tablet core adjacent to a source of powder coating material in such an electric field and with at least part of the core maintained at such a different electric potential from that of the coating material that the application of the electric potential difference causes the powder to be directed from the source of the powder towards the tablet core and a surface of the core to become coated with the powder coating material.

Because the coating of the tablet core involves the direction of powder material towards the tablet core as a result of the application of an electric field and an electric potential difference between at least part of the tablet core and the powder material, the destination of the powder material can be confined, at least primarily, to the surface of the core of the tablet, if that is arranged to be the only exposed surface that is in the vicinity of the powder material and at a suitable potential difference to the powder material.

A particular advantage of the method is that it can be carried out as a continuous process.

Advantageously, the tablet core is conveyed on a conveying means through a region adjacent to the source of powder coating material. By conveying the tablet core it is possible to ensure that the tablet core is handled delicately throughout the coating process so that even a fragile tablet core is not damaged.

The method may be employed to coat tablet cores that would be too fragile to withstand conventional tablet coating processes. Thus the invention enables tablets of conventional shape but of a wider range of compositions to be produced; also, tablets of unconventional shapes, for example having opposite flat faces rather than conventional domed faces, may be produced by the invention. Such flat-faced tablets are generally too fragile to be coated using conventional methods. Furthermore, the flat faces of the tablets often become joined together forming tablet twins or groups of tablets which do not then become properly coated when conventional coating methods are used.

The tablet core may be supported from above adjacent to the source of powder coating material and the powder may rise from the source upwards towards and onto a lower surface of the substrate.

The tablet core produced by the coating method defined above may be only partly coated and advantageously the method of coating includes the further step of supporting the coated tablet core adjacent to a source of powder coating material in such an electric field and with at least a part of the core maintained at such a different electric potential from that of the coating material that the application of the electric potential difference causes the powder to be directed from the source of the powder towards the tablet core and an uncoated surface of the core to be coated with the powder coating material. In that way a coating may easily be provided over the entire surface of the tablet core, and different coating materials may be used for coating different parts of the core. For example, a different coloured coating may be formed on each of the opposite faces of the tablet.

The first aspect of the invention still further provides a pharmaceutical tablet that has been electrostatically coated by a method as defined above.

The powder coating material and method of coating according to the first aspect of the invention has been developed specifically for coating of pharmaceutical tablet cores and to meet the stringent conditions imposed on the material because of that application. Having developed a material and method suitable for use in coating pharmaceutical tablet cores, we have also considered other applications in which the material and method could usefully be employed. For example, within the pharmaceutical industry the material and method may be employed to coat other pharmaceutical products not taken orally, for example, a pessary, a bougie or a suppository, or other pharmaceutical substrates.

Thus, according to a second aspect of the invention there is provided a powder coating material for use in the electrostatic powder coating of a pharmaceutical substrate, the material having one or more of the following properties:
 a) being edible by humans and/or animals,
 b) being made up of at least two different components, the particles preferably being composite particles, c) being fusible into a film coating at a temperature of less than 250° C. at atmospheric pressure,
d) at least 30% by volume of the particles having a particle size in the range of from 5 μm to 20 μm,
e) being susceptible to movement under the action of electrostatic forces, the susceptibility being determined by the test defined herein.

It is particularly advantageous that the powder coating material is a physiologically tolerable material and preferably a pharmaceutically acceptable material. As indicated above, that imposes severe constraints on the powder coating materials used.

The material may also have any of the other properties referred to above when describing materials for coating pharmaceutical tablet cores.

The invention also provides a method of producing powder coating material comprising at least two different components for use in the electrostatic coating of a substrate, the method including the step of co-processing the at least two different components.

The second aspect of the invention further provides a method of electrostatically coating a pharmaceutical substrate with a powder coating material as defined above.

Where reference is made to % by number of particles, for example the % by number of particles having a particular size, the particles will preferably also have that % by volume of particles of that size. Furthermore, where reference is made to % by volume of particles, the particles will preferably also have that % by weight of particles.

Figure 2:
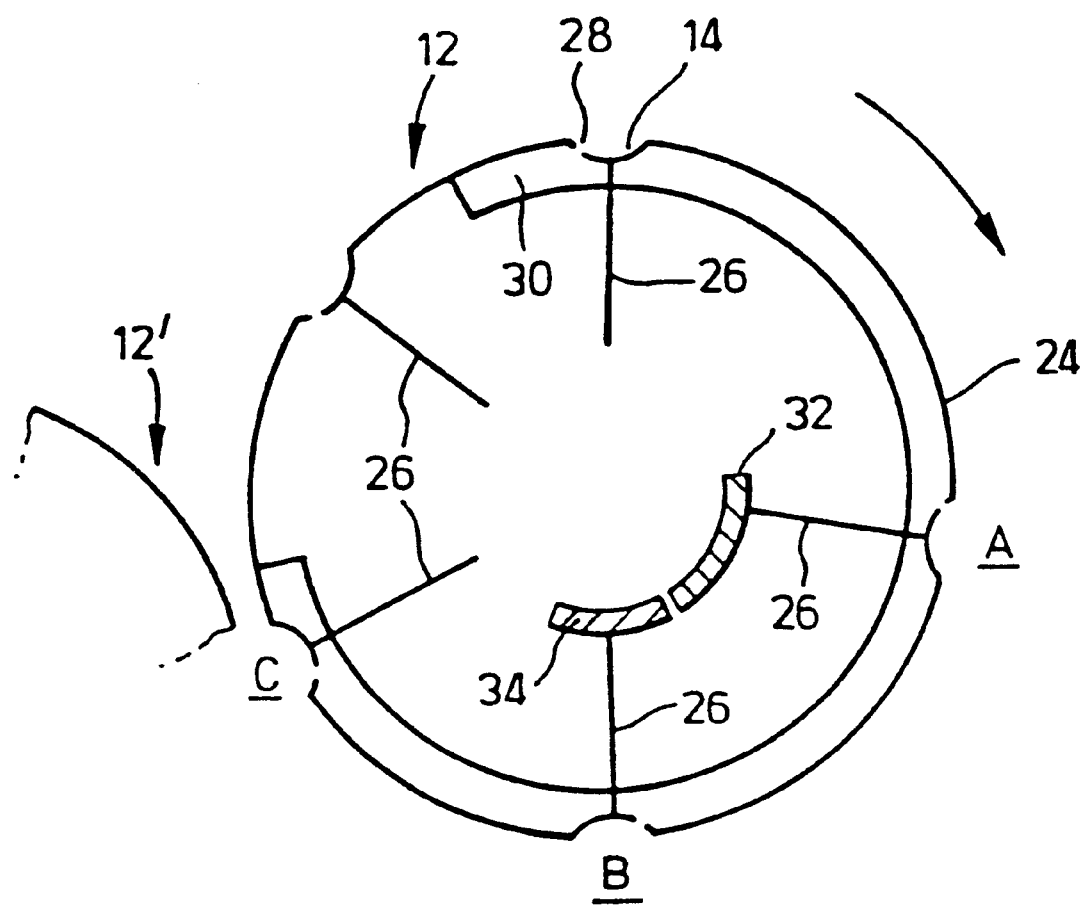

By way of example, a method of coating a core of a pharmaceutical tablet and certain powder coating materials suitable for use in coating cores of pharmaceutical tablets will now be described with reference to the accompanying drawings, in which:

FIG. 1 shows schematically a side view of an apparatus for coating a tablet core; and FIG. 2 shows schematically a cross-section of a drum of the apparatus of FIG. 1.

The apparatus shown schematically in FIG. 1 is for coating both faces of pharmaceutical tablet cores. The apparatus comprises an inclined tablet core feed chute 10 leading to a first rotatable drum 12. The drum 12 is of steel and has circular depressions 14 (FIG. 2) in its outer surface in each of which a core can be held by suction, as will be explained later.

The drum 12 is rotatable in the direction shown by the arrow. Adjacent to the circumference of the drum 12 downstream of the tablet feed chute 10 is a preconditioning station comprising an electrostatic spray gun 16, which causes exposed surfaces of the cores to be covered in charged droplets from the gun 16. Downstream of the preconditioning station is a coating station B comprising a vibrating powder tray 18 for holding, fluidising and re-circulating in the coating zone D the powder with which the cores are to be coated. Downstream of the coating station is a fusing station C comprising a heater 20. After the fusing station C, the coated core passes a cooling station, not shown, where cool air is directed over or around the core to cool the fused coating.

A second drum 12' is adjacent to the first drum 12, the nip between the drums being downstream of the fusing station C. The second drum 12' rotates in the opposite sense to the first drum 12, as indicated by the arrow. The second drum 12' is provided with a preconditioning station A' comprising a gun 16', a coating station B' comprising a powder tray 18', a fusing station C' comprising a heater 20' and a cooling station (not shown).

A core collection chute 22 is inclined downwardly away from the second drum 12' downstream of the fusing station C', taking coated cores to be further processed and packed.

The first drum 12 will be described in more detail with reference to FIG. 2. It comprises a rotatable shell 24, the outer face of which carries the depressions 14. In FIG. 2, only five exemplary depressions 14 are shown; it will be appreciated that in practice many more depressions will be evenly spaced in a circumferential row around the shell 24, and that there may be several circumferential rows across the width of the drum, whether formed by one continuous shell or several shells fixed side by side. The depressions 14 on the drums are shaped and dimensioned to ensure that the complete face of the core and half the depth of the side wall are exposed while the core is on the drum. In the case of a circular tablet core, a depression diameter close to that of the core diameter is preferred. In some applications, the depth of the depression should be such as to allow at least 50% of the core thickness to be exposed to the particles of the coating material so that exposure of first one face of the core and then the other leads to complete coverage of the core.

Each depression 14 is electrically insulated from the other depressions on the drum and is provided with a respective pick up arm 26 extending radially inward, toward but ending short of the centre of the drum. The pick up arms 26 are attached to the inner surface of the shell 24 and rotate with it. Each associated pick up arm 26 and depression 14 together make a moving electrode to charge a core in the depression. Each depression 14 has means for holding the core against forces such as gravity, for example a passage 28 through its wall which can be in communication with a suction manifold 30 which does not rotate with the shell and extends around a portion of the periphery of the drum interior from immediately upstream of the core feed chute 10 to adjacent to the nip between the first drum 12 and the second drum 12'.

A first, earthed, stationary arcuate electrode 32 is located inside the drum at an angular position corresponding to the preconditioning station A. A second stationary arcuate electrode 34 at a potential difference to earth is located inside the drum at an angular position corresponding to the coating station B. The outer arcuate surfaces of the stationary electrodes are at the same radial distance from the centre of the drum as the free ends of the pick up arms 26 of the moving electrodes. As the shell 24 rotates, the moving electrodes contact the first and second stationary electrodes sequentially. The drum 12 is held at the same potential difference to earth as the coating powder, preferably at earth potential, preferably by being connected to the powder tray 18.

The second drum 12' is constructed similarly to the first drum, comprising a rotatable shell with depressions, pick up arms and first and second stationary electrodes and a suction manifold. The angular locations of the first and second stationary electrodes correspond to the second preconditioning station A' and the second coating station B', and the suction manifold extends from immediately upstream of the nip between the two drums to adjacent to the core collection chute 22.

In use, cores are fed continuously to the core feed chute 10. A core passes down the core feed chute 10 into a depression 14 in the rotating shell 24 of the first drum 12. At that angular position, the depression overlies the suction manifold 30, and so the core is held in the depression by the suction through the passage 28 in the shell. The shell 24 continues to rotate bringing the core to the preconditioning station A, at which point the pick up arm 26 attached to the depression 14 contacts the first stationary electrode 32, earthing the moving electrode and thus the core held in the depression. As the earthed tablet core passes the electrostatic spray gun 16, its exposed surface is sprayed with charged droplets of a capture-enhancing liquid, for example polyethylene glycol.

The shell 24 continues to rotate, taking the moving electrode 26 out of contact with the first stationary electrode 32 and bringing it into contact with the second stationary electrode 34, as the tablet approaches the coating station B. The exposed polyethylene glycol treated core surface is now at a potential difference to earth, and coating powder material is directed to it from the powder tray 18 by virtue of electrostatic forces. The potential well generated by holding the surface of the drum and the powder at the same potential difference to earth as each other and the core at a different potential different to earth ensures that powder is attracted to the core but that the surface of the drum remains substantially free of powder.

The shell 24 continues to rotate, taking the moving electrode 26 out of contact with the second stationary electrode 34 and brings the core to the fusing station C, where the heater 20 fuses the powder on the coated surface of the core to form a continuous film.

As the shell 24 continues to rotate, the core leaves the fusing station C, passes through the cooling station (not shown), and the depression carrying the core no longer overlies the suction manifold 30. The core drops from the first drum 12 into a depression on the outer surface on the second drum 12', with its uncoated surface outermost on the drum 12'; the depression is in communication with the suction manifold 30 of the second drum. The coating of the core is completed as it travels through the second preconditioning A', coating B', fusing C' and cooling stations. The coating powder material at the second coating station may be the same as that at the first, or different. Thus, tablets having differently coated surfaces can be produced. As the coated tablet draws adjacent to the collection chute 22, the depression carrying it ceases to overlie the suction manifold, and the coated tablet falls into the chute and is further processed and packed.

The drums themselves are preferably at least 60 mm in diameter and not less than the minimum tablet diameter in width rotating at at least ½ r.p.m. The suction pressure in the suction manifolds is sufficient to hold the tablets against gravity, preferably between 0.2 and 0.6 Bar below atmospheric pressure.

In the electrostatic spray guns 16, 16' at the preconditioning stations A, A', a semi-conducting, non-volatile fluid, such as polyethylene glycol or an aqueous solution thereof is fed at a rate of 0.1 to 1 ml/min. to a steel capillary of internal diameter 0.05 to 2 mm. The capillary is connected to a current limited high voltage (up to 50 kV at 30 to 100 $\mu$A) potential difference to earth as each core on a drum passes the gun, and a mist of charged droplets is discharged from the capillary toward the core on the drum; since the cores on the drum are earthed at the preconditioning stations, the charged droplets are guided by the electric field between the capillary and the core to the exposed surface of the core, where they are captured. The cores may be held at a potential difference to earth at the preconditioning stations, providing that they are also at a potential difference to the capillaries. In this case, the first stationary arcuate electrode 32 is at a potential difference to earth. The supply of droplets from each capillary is controlled by switching the voltage off and earthing the capillary through a resistor (1 to 10 M$\Omega$) as each core leaves the preconditioning station; this ensures a sharp cut off of the droplets between tablet cores.

At coating stations B, B', powdered coating material is supplied by vibrating feeders to the vibrating trays 18, 18'. The level of the powder in the trays is determined by a levelling blade above each tray. The powder may be vibrofluidized and continuously re-circulated. The trays may be of a plastics material having an earthed metal strip under the arc swept by the tablet cores on the respective drums or they may be metallic trays. An alternative way to charge the particles is triboelectrical charging. The trays are preferably 50 to 150 mm long and 3 to 40 mm wide. If more than one tray is used, to provide a bi- or multi-coloured face or a face carrying more than one polymer composition, the tray dimensions will be appropriately different. The tablet cores are charged by a voltage of 3 to 15 kV current limited to 5 $\mu$A.

At the fusing or drying stations C, C', energy is imparted to the core surfaces to fuse the powder and provide a uniform coating on the exposed surface of the core. The energy is provided by focused radiation preferably in the infra-red region; the energy power requirement will be determined largely by the coating material. After fusing or drying, the coating is set by cooling, using an air blower.

Preferred coating apparatus according to the invention can coat up to 300,000 tablet cores each hour.

Examples of powder coating materials suitable for use in the method of coating tablet cores described above with reference to FIGS. 1 and 2 will now be given:

EXAMPLE 1

A dry powder coating material was prepared by the following method.

(a) A sample containing, by weight,

| | |
|---|---|
| 55.5% | Eudragit RS (Trade mark) (fine powdered ammonio-methacrylate copolymer) |
| 18.5% | polyethylene glycol (high molecular weight: approximately 20 000) |
| 15.0% | Titanium dioxide |
| 5.0% | Aluminium lake |
| 5.0% | Sodium lauryl sulphate |
| 0.5% | Explotab (Trade mark) (sodium starch glycolate) |
| 0.5% | Aerosil 200 (Trade mark) (colloidal silicon dioxide) | was premixed in a high shear mixer.

Before mixing, the particle sizes of the components of the sample were

| | |
|---|---|
| TiO$_2$ | 50% by volume less than 5 $\mu$m |
| Aluminium lake | 50% by volume less than 1 $\mu$m |
| Sodium lauryl sulphate | 50% by volume less than 100 $\mu$m |
| Eudragit | 50% by volume less than 40 $\mu$m |
| Polyethylene glycol | 50% by volume from 60 to 70 $\mu$m |

(b) The premixed mixture was wet granulated by the following method. Water was slowly added to the mixture obtained in (a) above in a high shear mixer for a few minutes until a granulated mixture was obtained. The weight of water added was between about 10 to 15% of the weight of the premixed mixture.

(c) The granulated mixture obtained in step (b) above was dried in a fluid bed drier at a temperature of approximately 45° C. for about 20 to 30 minutes to give a material having a moisture content (measured as loss on drying) below 3% by weight.

(d) The granules obtained in step (c) were impact milled and then micronised using a fluid energy mill to a powder containing particles having a size distribution such that 50% by volume of particles were of a size less than 20 μm, and almost 100% by volume were of a size less than 60 μm. The peak in the size distribution of the particles was seen at about 10 μm.

The powder was found to be susceptible to movement under the action of electrostatic forces as defined above.

(e) The powder was coated onto a tablet core using the method and apparatus described above. No pretreatment of capture-enhancing fluid was used. The powder coating on the tablet core surface was then fused using an infra red source to heat the coating material on the tablet core to a temperature above 130° C. for about 5 seconds. The resulting coating had good opacity, was smooth, glossy and brightly coloured. The thickness of the coating was found to be less than 100 μm.

The distribution of particle sizes of the particles of the powder produced in step (d) above was measured. The particle size distribution measured in volume %.

| | |
|---|---|
| 100% | less than 57.25 μm |
| 70.29% | less than 22.04 μm |
| 5.58% | less than 1.52 μm |

Approximately 50% of the particles had a size from 15.05 μm to 32.29 μm.

Approximately 35% of the particles had a size from 18.21 μm to 32.29 μm.

The average particle size was 19.17 μm (calculated as a mode).

EXAMPLE 2

A sample containing, by weight,

| | |
|---|---|
| 59.6% | Eudragit RS (ammonio-methacrylate copolymer) |
| 19.9% | Klucel (Trade mark) (hydroxy propyl cellulose) |
| 15.0% | Titanium dioxide |
| 5.0% | Aluminium lake |
| 0.5% | Croscarmellose sodium (cross-linked carboxymethylcellulose sodium) | was used to make a powder coating material by the method described in steps (a) to (d) of Example 1. The powder material was coated onto and fused on the surface of a tablet core as described in step (e) of Example 1. The resulting coating was smooth and highly glossy with strong colour and good opacity. The coating was judged to exhibit a higher gloss than would be expected for a conventional film-coated tablet.

EXAMPLE 3

A sample containing, by weight,

| | |
|---|---|
| 39.75% | Eudragit RS (ammonio-methacrylate copolymer) |
| 39.75% | Klucel (hydroxy propyl cellulose) |
| 15.0% | Titanium dioxide |
| 5.0% | Aluminium lake |
| 0.5% | Aerosil 200 (colloidal silicon dioxide) | was used to make a powder coating material by the method described in steps (a) to (d) of Example 1. The powder coating material was coated and fused on the surface of a tablet core as described in step (e) of Example 1. The resulting coating was smooth and glossy with strong colour and good opacity.

EXAMPLE 4

A sample containing, by weight,

| | |
|---|---|
| 60.0% | Eudragit RS (ammonio-methacrylate copolymer) |
| 20.0% | Glyceryl monostearate |
| 15.0% | Titanium dioxide |
| 5.0% | Aluminium lake | was used to make a powder coating material by the method described in steps (a) to (d) of Example 1. The powder material was coated and fused on the surface of a tablet core as described in step (e) of Example 1. The resulting coating was smooth and matt with strong colour and good opacity.

EXAMPLE 5

A sample containing, by weight,

| | |
|---|---|
| 60.0% | Eudragit RS (ammonio-methacrylate copolymer) |
| 20.0% | Xylitol |
| 15.0% | Titanium dioxide |
| 5.0% | Aluminium lake | was used to make a powder coating material by the method described in steps (a) to (d) of Example 1. The powder material was coated and fused on the surface of a tablet core as described in step (e) of Example 1. The resulting coating was semi-glossy with strong colour and good opacity.

EXAMPLE 6

A sample containing, by weight,

| | |
|---|---|
| 46.5% | Eudragit RS (ammonio-methacrylate copolymer) |
| 28.0% | Klucel (hydroxy propyl cellulose) |
| 15.0% | Titanium dioxide |
| 5.0% | Aluminium lake |
| 5.0% | Polyethylene glycol 6000 |
| 0.5% | Aerosil 200 (colloidal silicon dioxide) | was used to make a powder coating material by the method described in steps (a) to (d) of Example 1. The powder material was coated and fused on the surface of a tablet core as described in step (e) of Example 1. The resulting coating was smooth with strong colour and good opacity.

EXAMPLE 7

(a) A sample containing, by weight,

| | |
|---|---|
| 56.25% | polyethylene glycol |
| 20.0% | Titanium dioxide |
| 18.75% | Eudragit RS (ammonio-methacrylate copolymer) |
| 5.0% | Aluminium lake | was blended using a high shear mixer. Before blending, the polyethylene glycol and Eudragit were of similar particle size with at least 50% by volume of the particles having a size between from 100 µm to 200 µm and at least 50% by volume of the particles of Titanium dioxide and the Aluminium lake had a size less than 1 µm.

(b) The dry blended mixture was then milled to give a powder material having particle size less than 300 µm with at least 50% by volume of the particles having a size between from 100 µm to 200 µm.

(c) The material was coated onto tablet cores using the method and apparatus described above, including a pretreatment spray of polyethylene glycol. The powder coating on the tablet core surface was then fused using an infra red source to heat the coating material on the tablet core to a temperature above 130° C. for about 5 seconds. The resulting coating was smooth and highly glossy with strong colour and good opacity. The coating was judged to exhibit a higher gloss than would be expected for a conventional film-coated tablet.

EXAMPLE 8

A sample containing, by weight,

| | |
|---|---|
| 56.25% | polyoxyethylene glycol |
| 20.0% | Titanium dioxide |
| 18.75% | Eudragit RS (ammonio-methacrylate copolymer) |
| 5.0% | Aluminium lake | the components having similar particle size to those of Example 7 before blending (the polyoxyethylene having similar particle size to that of the Eudragit), was dry blended using a high shear mixer and the blended mixture was milled as described in step (b) of Example 7. The material obtained was coated onto tablet cores as described in step (c) of Example 7 and the resulting coating was smooth and highly glossy with strong colour and good opacity. The coating was judged to exhibit a higher gloss than would be expected for a conventional film-coated tablet.

Whilst in the examples described above, all of the components are in the form of solid particulate material, it should be understood that the powder coating material may include components which are in liquid form.

What is claimed is:

1. A method of electrostatically coating a pharmaceutical substrate with a powder material, which comprises electrostatically applying said powder material to said substrate, said powder material including composite particles, each composite particle comprising two or more components having different physical and/or chemical properties.

2. A method according to claim 1, in which at least 50% by weight of the particles of the powder material are composite particles.

3. A method according to claim 2, in which substantially all of the particles are composite particles.

4. A method according to claim 1, in which at least 30% by weight of the particles have a particle size which lies in a range from x to 2x, where x represents a size of particles in the powder.

5. A method according to claim 4, in which at least 30% by weight of the particles have a particle size which lies in a range from x to 1.5x.

6. A method according to claim 5, in which at least 30% by weight of the particles have a particle size which lies in a range from x to 1.25x.

7. A method according to claim 4, in which at least 75% by weight of the particles have the said particle size.

8. A method according to claim 1, in which at least 50% by volume of the particles of the powder material have a particle, size of at least 5 µm.

9. A method according to claim 8, in which at least 75% by volume of the particles have a particle size of at least 5 µm.

10. A method according to claim 9, in which at least 90% by volume of the particles of the powder material have a particle size of at least 5 µm.

11. A method according to claim 1, in which the powder material has a resistivity in the range of $10^8$ to $10^{16}$ Ωm.

12. A method according to claim 1, in which the powder material is able to be charged triboelectrically and/or by corona charging.

13. A method according to claim 1, in which the powder material is an electret or a magnet or a paramagnet.

14. A method according to claim 1, in which the powder material is susceptible to movement under the action of electrostatic forces.

15. A method according to claim 1, in which the powder material is treatable at a temperature of less than 250° C. to form a film coating.

16. A method according to claim 15, in which the powder material is treatable at a temperature of less than 200° C. to form a film coating.

17. A method according to claim 15, in which the powder material is able to be fused to form a film coating at a temperature of less than 250° C. at atmospheric pressure.

18. A method according to claim 17, in which the powder material is able to be fused to form a film coating at a temperature of less than 200° C. at atmospheric pressure.

19. A method according to claim 1, in which the powder material is fusible at a temperature in the range of 50° C. to 180° C.

20. A method according to claim 19, in which the powder material is fusible at a temperature in the range of 60° C. to 100° C.

21. A method according to claim 1, in which the powder material comprises a polymer which is curable to form a cross-linked polymer film.

22. A method according to claim 1, in which the powder material has a moisture content not more than 10% by weight based on the weight of the powder material.

23. A method according to claim 22, in which the powder material has a moisture content not more than 5% by weight based on the weight of the powder material.

24. A method according to claim 23, in which the powder material has a moisture content not more than 3% by weight based on the weight of the powder material.

25. A method according to claim 1, in which the powder material includes a first component which is fusible to form a continuous film on the surface of the tablet core.

26. A method according to claim 25, in which the first component is fusible into a film coating at a temperature of less than 250° C.

27. A method according to claim 26, in which the first component is fusible into a film coating at a temperature of less than 200° C.

28. A method according to claim 25, in which the first component is substantially soluble in aqueous media.

29. A method according to claim 25, in which the powder material includes at least 10% by weight of first component based on the weight of the powder material.

30. A method according to claim 29, in which the powder material includes at least 15% by weight of first component based on the weight of the powder material.

31. A method according to claim 30, in which the powder material includes at least 20% by weight of first component based on the weight of the powder material.

32. A method according to claim 25, in which the powder material further includes a second component which is able to be charged triboelectrically.

33. A method according to claim 25, in which the powder material further includes a second component which is an electret, or a magnet or a paramagnet.

34. A method according to claim 25, in which the powder material further includes a second component which is susceptible to movement under the action of electrostatic forces.

35. A method according to claim 31, in which the second component comprises one or more of the powder materials in the group consisting of acrylate and methacrylate polymers, polyalkenes, polyethylene oxides, polyvinyl alcohols and esters, and cellulose, cellulose ethers and cellulose esters.

36. A method according to claim 32, in which the powder material includes at least 10% by weight of second component based on the weight of the powder material.

37. A method according to claim 36 in which the powder material includes at least 20% by weight of second component based on the weight of the powder material.

38. A method according to claim 37, in which the powder material includes at least 40% by weight of second component based on the weight of the powder material.

39. A method according to claim 32, in which the powder material further includes a dispersing component.

40. A method according to claim 39, in which the dispersing component comprises a surfactant.

41. A method according to claim 39, in which the powder material includes at least 1% by weight of dispersing component based on the weight of the powder material.

42. A method according to claim 41, in which the powder material includes from 2 to 5% by weight of dispersing component based on the weight of the powder material.

43. A method according to claim 1, in which the powder material includes an anti-friction agent.

44. A method according to claim 1, in which the powder material includes a disintegrator.

45. A method according to claim 44, in which the powder material contains less than 1% by weight of disintegrator.

46. A method according to claim 1, in which the powder material includes components selected from opacifiers, colorants and flavorings.

47. A method according to claim 46, in which the powder material contains less than 10% by weight of opacifiers based on the weight of the powder material.

48. A method according to claim 46, in which the powder material contains less than 5% by weight of colorants and flavorings based on the weight of the material.

49. A method according to claim 1, in which the powder material includes a biologically active material.

50. A method according to claim 49, in which the powder material includes at least 0.5% by weight of active material based on the weight of the powder material.

51. A method according to claim 50, in which the powder material includes at least 1% by weight of active material based on the weight of the powder material.

52. A method according to claim 1, the method comprising supporting the substrate adjacent to a source of the powder material with a surface of the substrate at such a different electric potential from the coating material that the powder is caused to move from the source of the powder towards the substrate and the surface of the substrate becomes coated with the powder material.

53. A method according to claim 52, in which the method is carried out as a continuous process.

54. A method according to claim 52, in which the substrate is conveyed on a conveying means through a region adjacent to the source of powder material.

55. A method according to claim 52, in which the substrate is charged when the substrate is adjacent the source of powder material.

56. A method according to claim 55, in which the source of powder material is earthed.

57. A method according to claim 52, in which the substrate is supported from above and the powder moves from the source upwards towards a lower surface of the substrate.

58. A method according to claim 52, in which, before the substrate is supported adjacent to the source of powder material, a pretreatment composition is applied to said surface of the substrate.

59. A method according to claim 58, in which the pretreatment composition is a liquid.

60. A method according to claim 59, in which the liquid is polyethylene glycol.

61. A method according to claim 52, in which the method further includes the step that after the said surface of the substrate has been coated with the powder, the powder is treated to form a continuous film coating secured to the substrate.

62. A method according to claim 51, in which the method further includes the steps of supporting the coated substrate adjacent a source of powder material with an uncoated surface of the substrate exposed and with the uncoated surface of the substrate at a different electric potential from that of the coating material whereby the powder is caused to move from the source of the powder towards the substrate such that the exposed surface of the substrate becomes coated with the powder material.

63. A method according to claim 1, in which the substrate is a core of a pharmaceutical tablet.

64. A method according to claim 63, in which the core is of conventional shape.

65. A method of electrostatically coating a pharmaceutical substrate with a powder material, which comprises electrostatically applying said powder material to said substrate, wherein said powder material includes composite particles, each composite particle comprising two or more components having different physical and/or chemical properties, and wherein at least 30% by volume of the particles of the powder have the particle size in the range of from 5 $\mu$m to 25 $\mu$m.

66. A method according to claim 65, wherein the powder material contains active material.

67. A method according to claim 65, wherein the substrate is a core of a pharmaceutical tablet.

68. A method of electrostatically coating a pharmaceutical substrate with a powder material, which comprises electrostatically applying said powder material to said substrate, wherein said powder material includes composite particles, each composite particle comprising two or more components having different physical and/or chemical properties, and wherein at least 95% by number of the particles of the powder material have a particle size of less than 50 $\mu$m.

69. A method according to claim 68, in which at least 95% by number of the particles of the powder material have a particle size of less than 30 $\mu$m.

70. A method according to claim 68, wherein the powder material contains active material.

71. A method according to claim 68, wherein the substrate is a core of a pharmaceutical tablet.

72. A method of coating a tablet substrate, which is a core for a pharmaceutical tablet, which comprises electrostatically applying a powder material comprising active material to a surface of the core, wherein the powder material includes composite particles, each composite particle comprising two or more components having different physical and/or chemical properties.

73. A method according to claim 72, in which the powder material includes at least 0.5% by weight of active material based on the weight of the powder material.

74. A method according to claim 73, in which the powder material includes at least 1% by weight of active material based on the weight of the powder material.

75. A method according to claim 72, in which at least 50% by weight of the particles of the powder material are composite particles.

76. A method according to claim 75, in which substantially all of the particles are composite particles.

77. A method according to claim 72, in which at least 30% by weight of the particles have a particle size which lies in a range from x to 2x, where x represents a size of particles in the powder.

78. A method according to claim 77, in which at least 30% by weight of the particles have a particle size which lies in a range from x to 1.5x.

79. A method according to claim 78, in which at least 30% by weight of the particles have a particle size which lies in a range from x to 1.25x.

80. A method according to claim 77, in which at least 75% by weight of the particles have the said particle size.

81. A method according to claim 72, in which at least 50% by volume of the particles of the powder material have a particle size of at least 5 μm.

82. A method according to claim 81, in which at least 75% by volume of the particles have a particle size of at least 5 μm.

83. A method according to claim 82, in which at least 90% by volume of the particles of the powder material have a particle size of at least 5 μm.

84. A method according to claim 72, in which the powder material has a resistivity, in the range of $10^8$ to $10^{16}$ Ωm.

85. A method according to claim 72, in which the powder material is able to be charged triboelectrically and/or by corona charging.

86. A method according to claim 72, in which the powder material is an electret or a magnet or a paramagnet.

87. A method according to claim 72, in which the powder material is susceptible to movement under the action of electrostatic forces.

88. A method according to claim 72, in which the powder material is treatable at a temperature of less than 250° C. to form a film coating.

89. A method according to claim 88, in which the powder material is treatable at a temperature of less than 200° C. to form a film coating.

90. A method according to claim 88, in which the powder material is able to be fused to form a film coating at a temperature of less than 250° C. at atmospheric pressure.

91. A method according to claim 90, in which the powder material is able to be fused to form a film coating at a temperature of less than 200° C. at atmospheric pressure.

92. A method according to claim 72, in which the powder material is fusible at a temperature in the range of 50° C. to 180° C.

93. A method according to claim 92, in which the powder material is fusible at a temperature in the range of 60° C. to 100° C.

94. A method according to claim 72, in which the powder material comprises a polymer which is curable to form a cross-linked polymer film.

95. A method according to claim 72, in which the powder material has a moisture content not more than 10% by weight based on the weight of the powder material.

96. A method according to claim 95, in which the powder material has a moisture content not more than 5% by weight based on the weight of the powder material.

97. A method according to claim 96, in which the powder material has a moisture content not more than 3% by weight based on the weight of the powder material.

98. A method according to claim 72, in which the powder material includes a first component which is fusible to form a continuous film on the surface of the tablet core.

99. A method according to claim 98, in which the first component is fusible into a film coating at a temperature of less than 250° C.

100. A method according to claim 99, in which the first component is fusible into a film coating at a temperature of less than 200° C.

101. A method according to claim 98, in which the first component is substantially soluble in aqueous media.

102. A method according to claim 98, in which the powder material includes at least 10% by weight of first component based on the weight of the powder material.

103. A method according to claim 102, in which the powder material includes at least 15% by weight of first component based on the weight of the powder material.

104. A method according to claim 103, in which the powder material includes at least 20% by weight of first component based on the weight of the powder material.

105. A method according to claim 98, in which the powder material further includes a second component which is able to be charged triboelectrically.

106. A method according to claim 105, in which the second component comprises one or more of the powder materials in the group consisting of acrylate and methacrylate polymers, polyalkenes, polyethylene oxide, polyvinyl alcohols and esters, and cellulose, cellulose ethers and cellulose esters.

107. A method according to claim 105, in which the powder material includes at least 10% by weight of second component based on the weight of the powder material.

108. A method according to claim 107, in which the powder material includes at least 20% by weight of second component based on the weight of the powder material.

109. A method according to claim 108, in which the powder material includes at least 40% by weight of second component based on the weight of the powder material.

110. A method according to claim 105, in which the powder material includes a dispersing component.

111. A method according to claim 110, in which the dispersing component comprises a surfactant.

112. A method according to claim 110, in which the powder material includes at least 1% by weight of dispersing component based on the weight of the powder material.

113. A method according to claim 112, in which the powder material includes from 2 to 5% by weight of dispersing component based on the weight of the powder material.

114. A method according to claim 98, in which the powder material further includes a second component which is an electret, or a magnet or a paramagnet.

115. A method according to claim 98, in which the powder material further includes a second component which is susceptible to movement under the action of electrostatic forces.

116. A method according to claim 72, in which the powder material includes an anti-friction agent.

117. A method according to claim 72, in which the powder material includes a disintegrator.

118. A method according to claim 117, in which the powder material contains less than 1% by weight of disintegrator.

119. A method according to claim 72, in which the powder material includes components selected from opacifiers, colourants and flavourings.

120. A method according to claim 119, in which the powder material contains less than 10% by weight of opacifiers based on the weight of the powder material.

121. A method according to claim 120, in which the powder material contains less than 5% by weight of colourants and flavourings based on the weight of the powder material.

122. A method according to claim 72, the method comprising supporting the tablet core adjacent to a source of the powder material with a surface of the tablet core at such a different electric potential from that of the powder material that is caused the powder to move from the source of the powder towards the tablet core and the surface of the tablet core becomes coated with the powder material.

123. A method according to claim 122, in which the method is carried out as a continuous process.

124. A method according to claim 122, in which the tablet core is conveyed on a conveying means through a region adjacent to the source of powder material.

125. A method according to claim 122, in which the tablet core is charged when the tablet core is adjacent the source of powder material.

126. A method according to claim 125, in which the source of powder material is earthed.

127. A method according to claim 122, in which the tablet core is supported from above and the powder moves from the source upwards towards a lower surface of the tablet core.

128. A method according to claim 122, in which, before the tablet core is supported adjacent to the source of powder material, a pretreatment composition is applied to said surface of the tablet core.

129. A method according to claim 128, in which the pretreatment composition is a liquid.

130. A method according to claim 129, in which the liquid is polyethylene glycol.

131. A method according to claim 122, in which the method further includes the step that after the said surface of the tablet core has been coated with the powder, the powder is treated to form a continuous film coating secured to the tablet core.

132. A method according to claim 122, in which the method further includes the steps of supporting the coated substrate adjacent a source of powder material with an uncoated surface of the tablet core exposed and with said surface of the tablet core at a different electric potential from that of the coating material whereby the application of the electric potential causes the powder to move from the source of the powder towards the tablet core such that the exposed surface of the tablet core becomes coated with the powder material.

133. A method according to claim 72, in which the core is of conventional shape.

134. A method according to claim 72, in which the quantity of powder material applied to the tablet core amounts to substantially one dose of active material.

135. A method according to claim 72, in which the active material is one or more compounds selected from acid-peptic and motility-influencing agents, laxatives, anti-diarrhoeials, colo-rectal agents, pancreatic enzymes and bile acids, antiarrhythmics, antianginals, diuretics, anti-hypertensives, anticoagulants, anti-thrombotics, fibrinolytics, haemostatics, hypolipidaemic agents, anti-anaemia agents, neutropenia agents, hypnotics, anxiolytics, anti-psychotics, antidepressants, anti-emetics, anti-convulsants, CNS stimulants, analgesics, antipyretics, anti-migraine agents, non-steroidal anti-inflammatory agents, anti-gout agents, muscle relaxants, neuro-muscular agents, steroids, hypoglycaemic agents, hyperglycaemic agents, diagnostic agents, antibiotics, anti-fungals, anti-malarials, anti-virals, immunosuppressants, nutritional agents, vitamins, electrolytes, anorectic agents, appetite suppressants, bronchodilators, expectorants, antitussives, mucolytics, decongestants, anti-glaucoma agents, oral contraceptive agents, diagnostic and anti-neoplastic agents.

136. A method according to claim 72, in which the tablet core contains no active material.

137. A method according to claim 72, in which the tablet core contains the same active material as the powder material.

138. A method according to claim 72, in which the tablet core contains a different active material from the powder material.

139. A method according to claim 72, in which the tablet core contains no active material.

140. A method according to claim 72, in which the tablet core contains the same active material as the powder material.

141. A method according to claim 72, in which the tablet core contains a different active material from the powder material.

142. A method of coating a tablet substrate, which is a core for a pharmaceutical tablet, which comprises electrostatically applying a powder material comprising active material to a surface of the core, at least 30% by volume of the particles of the powder having a particle size in the range of from 5 $\mu$m to 25 $\mu$m.

143. A method according to claim 142, wherein the tablet contains no active material.

144. A method according to claim 142, wherein the tablet core contains the same active material as the powder material.

145. A method according to claim 142, wherein the tablet core contains a different active material from the powder material.

146. A method according to claim 142, wherein the powder material includes composite particles, each composite particle comprising two or more components having different physical and/or chemical properties.

147. A method of coating a tablet substrate, which is a core for a pharmaceutical tablet, which comprises electrostatically applying a powder material comprising active material to a surface of the core, at least 95% by number of the particles of the powder material having a particle size of less than 50 $\mu$m.

148. A method according to claim 147, in which at least 95% by number of the particles of the powder material have a particle size of less than 30 $\mu$m.

149. A method according to claim 147, wherein the tablet core contains no active material.

150. A method according to claim 147, wherein the table core contains the same active material as the powder material.

151. A method according to claim 147, wherein the tablet core contains a different active material from the powder material.

152. A method according to claim 147, wherein the powder material includes composite particles, each composite particle comprising two or more components have different physical and/or chemical properties.

153. A method of electrostatically coating a substrate with a powder material, which comprises electrostatically applying said powder material to said substrate, said substrate being in the form of a tablet, and the powder material including composite particles, each composite particle comprising two or more components having different physical and/or chemical properties.

154. A method according to claim 153, in which at least 50% by weight of the particles of the powder material are composite particles.

155. A method according to claim 154, in which substantially all of the particles are composite particles.

156. A method according to claim 153, in which at least 30% by weight of the particles have a particle size which lies in a range from x to 2x, where x represents a size of particles in the powder.

157. A method according to claim 156, in which at least 30% by weight of the particles have a particle size which lies in a range from x to 1.5x.

158. A method according to claim 157, in which at least 30% by weight of the particles have a particle size which lies in a range from x to 1.25x.

159. A method according to claim 156, in which at least 75% by weight of the particles have the said particle size.

160. A method according to claim 153, in which at least 50% by volume of the particles of the powder material have a particle size of at least 5 µm.

161. A method according to claim 160, in which at least 75% by volume of the particles have a particle size of at least 5 µm.

162. A method according to claim 153, in which at least 90% by volume of the particles of the powder material have a particle size of at least 5 µm.

163. A method according to claim 153, in which the powder material has a resistivity, in the range of $10^8$ to $10^{16}$ Ωm.

164. A method according to claim 153, in which the powder material is able to be charged triboelectrically and/or by corona charging.

165. A method according to claim 153, in which the powder material is an electret or a magnet or a paramagnet.

166. A method according to claim 153, in which the powder material is susceptible to movement under the action of electrostatic forces.

167. A method according to claim 153, in which the powder material is treatable at a temperature of less than 250° C. to form a film coating.

168. A method according to claim 167, in which the powder material is treatable at a temperature of less than 200° C. to form a film coating.

169. A method according to claim 168, in which the powder material is able to be fused to form a film coating at a temperature of less than 250° C. at atmospheric pressure.

170. A method according to claim 169, in which the powder material is able to be fused to form a film coating at a temperature of less than 200° C. at atmospheric pressure.

171. A method according to claim 153, in which the powder material is fusible at a temperature in the range of 50° C. to 180° C.

172. A method according to claim 171, in which the powder material is fusible at a temperature in the range of 60° C. to 100° C.

173. A method according to claim 153, in which the powder material comprises a polymer which is curable to form a cross-linked polymer film.

174. A method according to claim 153, in which the powder material has a moisture content not more than 10% by weight based on the weight of the powder material.

175. A method according to claim 174, in which the powder material has a moisture content not more than 5% by weight based on the weight of the powder material.

176. A method according to claim 175, in which the powder material is a moisture content not more than 3% by weight based on the weight of the powder material.

177. A method according to claim 153, in which the powder material includes a first component which is fusible to form a continuous film on the surface of the substrate.

178. A method according to claim 177, in which the first component is fusible into a film coating at a temperature of less than 250° C.

179. A method according to claim 178, in which the first component is fusible into a film coating at a temperature of less than 200° C.

180. A method according to claim 177, in which the first component in substantially soluble in aqueous media.

181. A method according to claim 177, in which the powder material includes at least 10% by weight of first component based on the weight of the powder material.

182. A method according to claim 177, in which the powder material includes at least 15% by weight of first component based on the weight of the powder material.

183. A method according to claim 182, in which the powder material includes at least 20% by weight of first component based on the weight of the powder material.

184. A method according to claim 177, in which the powder material further includes a second component which is able to be charged triboelectrically.

185. A method according to claim 177, in which the powder material further includes a second component which is an electret, or a magnet or a paramagnet.

186. A method according to claim 177, in which the powder material further includes a second component which is susceptible to movement under the action of electrostatic forces.

187. A method according to claim 184, in which the second component comprises one or more of the powder materials in the group consisting of acrylate and methacrylate polymers, polyalkenes, polyethylene oxide, polyvinyl alcohols and esters, and cellulose, cellulose ethers and cellulose esters.

188. A method according to claim 184, in which the powder material includes at least 10% by weight of second component based on the weight of the powder material.

189. A method according to claim 188, in which the powder material includes at least 20% by weight of second component based on the weight of the powder material.

190. A method according to claim 189, in which the powder material includes at least 40% by weight of second component based on the weight of the powder material.

191. A method according to claim 184, in which the powder material further includes a dispersing component.

192. A method according to claim 191, in which the dispersing component comprises a surfactant.

193. A method according to claim 191, in which the powder material includes at least 1% by weight of dispersing component based on the weight of the powder material.

194. A method according to claim 193, in which the powder material includes from 2 to 5% by weight of dispersing component based on the weight of the powder material.

195. A method according to claim 153, in which the powder material includes an anti-friction agent.

196. A method according to claim 153, in which the powder material includes a disintegrator.

197. A method according to claim 196, in which the powder material contains less than 1% by weight of disintegrator.

198. A method according to claim 152, in which the powder material includes components selected from opacifiers, colourants and flavourings.

199. A method according to claim 198, in which the powder material contains less than 10% by weight of opacifiers based on the weight of the powder material.

200. A method according to claim 198, in which the powder material contains less than 5% by weight of colourants and flavourings based on the weight of the powder material.

201. A method according to claim 153, the method comprising supporting the substrate adjacent to a source of the powder material with a surface of the substrate maintained at such said different electric potential from that of the coating material that the application of the electric potential causes the powder to move from the source of the powder towards the substrate and the surface of the substrate becomes coated with the powder material.

202. A method according to claim 201, in which the method is carried out as a continuous process.

203. A method according to claim 201, in which the substrate is conveyed on a conveying means through a region adjacent to the source of powder material.

204. A method according to claim 201, in which the substrate is charged when the substrate is adjacent the source of powder material.

205. A method according to claim 204, in which the source of powder material is earthed.

206. A method according to claim 201, in which the substrate is supported from above and the powder moves from the source upwards towards a lower surface of the substrate.

207. A method according to claim 201, in which, before the substrate is supported adjacent to the source of powder material, a pretreatment composition is applied to a surface of the substrate.

208. A method according to claim 207, in which the pretreatment composition is a liquid.

209. A method according to claim 208, in which the liquid is polyethylene glycol.

210. A method according to claim 201, in which the method further includes the step that after the said surface of the substrate has been coated with the powder, the powder is treated to form a continuous film coating secured to the substrate.

211. A method according to claim 201, in which the method further includes the steps of supporting the coated substrate adjacent a source of powder material with an uncoated surface of the substrate exposed and with a surface of the substrate at a different electric potential from that of the powder material whereby is caused the powder to move from the source of the powder towards the substrate such that the exposed surface of the substrate becomes coated with the powder material.

212. A method according to claim 153, wherein the powder material applied contains active material.

213. A method of electrostatically coating a substrate with a powder material, the substrate being in the form of a tablet, which comprises electrostatically applying said powder material to said substrate, wherein said powder material includes composite particles, each composite particle comprising two or more components having different physical and/or chemical properties, and wherein at least 30% by volume of the particles of the powder have the particle size in the range of from 5 $\mu$m to 25 $\mu$m.

214. A method according to claim 213, wherein the powder material applied contains active material.

215. A method of electrostatically coating a substrate with a powder material, the substrate being in the form of a tablet, which comprises electrostatically applying said powder to said substrate, wherein said powder material includes composite particles, each composite particle comprising two or more components having different physical and/or chemical properties, and wherein at least 95% by number of the particles of the powder material have a particle size of less than 50 $\mu$m.

216. A method according to claim 215, in which at least 95% by number of the particles of the powder material have a particle size of less than 30 $\mu$m.

217. A method according to claim 215, wherein the powder material applied contains active material.

218. A method of coating a substrate which is a core for a pharmaceutical dosage form, which comprises electrostatically applying to a surface of the core a powder material comprising active material, the quantity of coating material applied constituting substantially one dosage of active material, wherein the powder material includes composite particles, each composite particle comprising two or more components having different physical and/or chemical properties.

219. A method according to claim 218, in which the core of the pharmaceutical dosage form contains no active material.

220. A method according to claim 218, in which the core of the pharmaceutical dosage form contains the same active material as the powder material.

221. A method according to claim 218, in which the pharmaceutical dosage form contains a different active material from the powder material.

222. A method according to claim 218, in which the pharmaceutical dosage form contains no active material.

223. A method according to claim 218, in which the pharmaceutical dosage form contains the same active material as the powder material.

224. A method according to claim 218, in which the pharmaceutical dosage form contains a different active material from the powder material.

225. A method according to claim 218, the method comprising supporting the substrate adjacent to a source of the powder material with a surface of the substrate at such a different electric potential from that of the coating material that the powder is caused to move from the source of the powder towards the substrate and the surface of the substrate becomes coated with the powder material.

226. A method according to claim 218, wherein the method further includes the step that after the said surface of the substrate has been coated with the powder, the powder is treated to form a continuous film coating secured to the substrate.

227. A method according to claim 218, wherein the method further includes the steps of supporting the coated substrate adjacent a source of powder material with an uncoated surface of the substrate exposed with the uncoated surface of the substrate at a different electric potential from that of the coating material whereby the powder is caused to move from the source of the powder towards the substrate such that the exposed surface of the substrate becomes coated with the powder material.

228. A method of coating a substrate, which is a core for a pharmaceutical dosage form, which comprises electrostatically applying to a surface of the core a powder material comprising active material, the quantity of coating material applied constituting substantially one dosage of active material, wherein at least 30% by volume of the particles of the powder have a particle size in the range of from 5 $\mu$m to 25 $\mu$m.

229. A method according to claim 228, wherein the core of the dosage form contains no active material.

230. A method according to claim 228, wherein the core of the dosage form contains the same active material as the powder material.

231. A method according to claim 228, wherein the core of the dosage form contains a different active material from the powder material.

232. A method according to claim 228, wherein the powder material includes composite particles, each composite particle comprising two or more components having different physical and/or chemical properties.

233. A method of coating a substrate, which is a core of a pharmaceutical dosage form, which comprises electrostatically applying to a surface of the core a powder material comprising active material, the quantity of coating material applied constituting substantially one dosage of active material, wherein at least 95% by number of the particles of the powder material have a particle size of less than 50 μm.

234. A method according to claim 233, wherein the core of the dosage form contains no active material.

235. A method according to claim 233, wherein the core of the dosage form contains the same active material as the powder material.

236. A method according to claim 233, wherein the core of the dosage form contains a different active material from the powder material.

237. A method according to claim 233, wherein the powder material includes composite particles, each composite particle comprising two or more components having different physical and/or chemical properties.

238. A method of coating a substrate which is a core of a pharmaceutical dosage form, which comprises electrostatically applying to the core a powder material comprising active material, wherein the coated substrate constitutes a unit dosage, and wherein the powder material includes composite particles, each composite particle comprising two or more components having different physical and/or chemical properties.

* * * * *